United States Patent [19]

Su et al.

[11] Patent Number: 5,262,421

[45] Date of Patent: Nov. 16, 1993

[54] USE OF DICENTRINE AND ITS DERIVATIVES FOR THE TREATMENT OF HYPERTENSION, ARRHYTHMIA, THROMBOSIS AND ATHEROSCLEROSIS

[75] Inventors: Ming-Jai Su; Chien-Chih Chen; Che-Ming Teng; Sheu-Meei Yu, all of Taipei, Taiwan

[73] Assignee: National Science Council, Taipei, Taiwan

[21] Appl. No.: 801,275

[22] Filed: Dec. 2, 1991

[51] Int. Cl.$^5$ .................... A61K 31/21; A61K 35/78
[52] U.S. Cl. ................................ 514/280; 424/195.1
[58] Field of Search ..................... 424/195.1; 514/463, 514/280

[56] References Cited

U.S. PATENT DOCUMENTS 4,543,256  9/1985  Neumeyer ........................ 514/280

OTHER PUBLICATIONS

Che-Ming Teng . . . "Dicentrine . . . from Lindera" Br. J. Pharmacol. 104(3):651-656 Oct. 1991.
Kondo et al. "Suppression of tumor cell . . . by . . . dicentrine" Biological Abs. 90(12): 137154 1990.
Kato et al ". . . crude extract of Linderae . . . on . . . cardiovascular system" Biological Abs. 76(2):12861 (1982).
Lu et al. "Studies . . Alkaloids *Lindera*" Yakugaku Zasshi 92(7) 910-917 (1972).

*Primary Examiner*—Frederick E. Waddell
*Assistant Examiner*—Gregory Hook
*Attorney, Agent, or Firm*—Marks & Murase

[57] ABSTRACT

A method for the treatment of hypertension, arrhythmia, thrombosis or/and atherosclerosis with an effective amount of dicentrine or other alkaloids extracted from *Lindera oldhammii* (*megaphylla*) Hemsl.

4 Claims, No Drawings

USE OF DICENTRINE AND ITS DERIVATIVES FOR THE TREATMENT OF HYPERTENSION, ARRHYTHMIA, THROMBOSIS AND ATHEROSCLEROSIS

BACKGROUND OF THE INVENTION

Hypertension is defined by American Heart Association as arterial blood pressure higher than 140/90 mmHg and by the World Health Organization (WHO) as higher than 160/95 mmHg. The prevalence of hypertension in the world population is estimated at approximately 20% of all adults. No single mechanism has been identified to explain the phenomenon of hypertension, but it may result from genetic factors. This type of hypertension is designated essential hypertension and includes most of the known cases. Several cardiovascular diseases are common or more severe in humans with high blood pressure, including atherosclerosis, coronary artery disease, congestive heart failure, stroke, diabetes, and renal and retinal diseases. The purpose of the treatment of hypertension is to prevent these significant cardiovascular complications. Most importantly, effective drug therapy has been shown through controlled clinical trials to reduce the morbidity and mortality associated with high arterial pressure. Antihypertensive drugs can be divided into seven classes, i.e., diuretics, $\beta$-blockers, centrally acting sympatholytics ($\alpha_2$-agonists), peripherally acting sympatholytics ($\alpha_1$-antagonists), calcium-channel blockers, orally active vasodilators and converting enzyme inhibitors. However, many side effects are observed during clinical applications of these antihypertensive agents.

Cardiac arrhythmia is a disorder of rate, rhythm, or conduction of electrical impulses within the heart. Such disorders are often associated with coronary artery diseases, e.g., myocardial infarction and atherosclerotic heart disease. Arrhythmia can eventually cause a decrease in the mechanical efficiency of the heart, reducing cardiac output. As a result, arrhythmia can have life-threatening effects that require immediate intervention. Many antiarrhythmic drugs act by blocking myocardial $Na^+$ or $Ca^{++}$ ion channels or by prolonging the cardiac action potential duration through the inhibition of potassium currents which are responsible for action potential repolarization.

Thrombosis is formed by the interaction of the damaged blood vessel wall with the blood components such as platelets and other clotting proteins. The damaged blood vessel is usually caused by elevated level of plasma cholesterol or triglyceride. When a blood vessel is damaged, the endothelium is disrupted and an underlying layer of collagen fiber is exposed. The exposed collagen attracts platelets and causes the release of ADP and the formation of thromboxane $A_2$ which further activate platelets. Platelet aggregation is one of the main causes leading to myocardial infarction and cerebral thrombosis. In spite of the intensive research for an effective antiplatelet drug, there is no drug to date that can effectively prevent the thrombosis, except for some old drugs, such as aspirin and dipyridamole.

Lu et al. isolated dicentrine and other alkaloids from the plant Lindera oldhamii (megaphylla) Hemsl (Yakugaku Zasshi, 92; 910–917, 1972), but they did not show any biological activity of these compounds.

SUMMARY OF THE INVENTION

It is an object of the present invention to provide an pharmaceutical composition which comprises an effective amount of dicentrine or other alkaloids extracted from Lindera oldhamii (megaphylla) Hemsl for the treatment of hypertension, arrhythmia, thrombosis and atherosclerosis.

For achieving the above-mentioned object, in a large scale screening test, we found ethylacetate soluble fractions of Lindera oldhamii (megaphylla) Hemsl possess platelet inhibition, vasorelaxation and antiarrhythmic action. These fractions inhibited the aggregation of washed rabbit platelets induced by ADP, collagen, arachidonic acid and platelet-activating factor (PAF). They also inhibited norepinephrine-induced contraction of rat thoracic aortae. Furthermore, the action potential of rat ventricular cells was prolonged by these fractions. After rechromatography on a silica gel column with n-hexane-ethylacetate (2:1), four potent compounds, dicentrine, N-methylnandigerine, N-methylovigenine and dicentrinone were obtained.

DESCRIPTION OF THE INVENTION

According to the present invention, dicentrine was found to be the most potent vasorelaxant in rat thoracic aorta. It is an $\alpha_1$-adrenoceptor antagonist as revealed by its competitive antagonism of norepinephrine- or phenylephrine-induced vasoconstriction of rat aortae. These effects still persisted in denuded aortae. It did not affect the aortic contraction induced by thromboxane receptor agonist U-46619, angiotensin II, high potassium or carbachol. Contraction of guinea-pig trachea caused by histamine or carbachol was slightly inhibited, while $\beta$-adrenoceptor relaxation to isoprenaline in trachea was not affected. In anesthetized rats, i.v. bolus of dicentrine (0.1–1.0 mg/kg) caused a dose-related reduction in mean arterial blood pressure, which reached a maximum reduction within 5 to 10 min after injection and persisted throughout a 2 hr observation period. The hypotensive activity of dicentrine was completely abolished after $\alpha_1$-adrenoceptor blockade. In conscious spontaneously hypertensive (SH) and normotensive (NT) rats, dicentrine also evoked dose-related decreases in mean arterial pressure which were of a greater magnitude in SH rats than in NT rats. With oral administration to conscious SH rats, the hypotensive effect persisted over 15 hr. In rats fed with a cholesterol-triglyceride-rich diet, the contractile force of the aorta increased to twice that of rats fed with a normal diet. Dicentrine not only decreased the serum triglyceride level but also restored the contractile force of cholesterol-triglyceride-treated rat aortae back to normal values.

In rat ventricular cells, the effects of dicentrine on action potential and membrane current were studied. At a stimulation frequency of 0.1 Hz, dicentrine prolonged the action potential, increased the time to peak and reduced the initial upstroke amplitude. Voltage clamp studies revealed that the prolongation of action potential by dicentrine was associated with a significant inhibition of both transient outward and steady state outward current. However, calcium current was less affected. The inhibition of the upstroke amplitude by dicentrine was correlated with its inhibition of fast sodium inward current. These results indicate that dicentrine may exert antiarrhythmic action.

The active compounds of this invention can be administered by any conventional means available for use in conjunction with pharmaceuticals; either as individual therapeutically active ingredient or in a combination of therapeutically active ingredients. Ordinarily, 1 to 10 mg per day is effective to obtain desired results. The active ingredients can be admixed with a pharmaceutically acceptable diluent and carrier, so that it can be administered orally in solid dosage forms, such as capsules, tablets, and powders, or in liquid dosage forms, such as elixirs, syrups, and suspensions; it can also be administered parenterally, in sterile liquid dosage forms.

The following examples serve to demonstrate the pharmacological activities of the claimed compounds. These examples are not intended as limiting since numerous modifications and varieties thereof will be apparent to those skilled in the art.

EXAMPLE 1

500 g of dried, ground root material Lindera oldhamii (megaphylla) Hemsl was extracted with 95% ethanol, and the extract was concentrated in vacuo and fractionated into ethanol- and ethylacetate-soluble fractions. The ethylacetate-soluble fraction was then applied to a column of silica gel and eight fractions were obtained. As shown in Table 1, many fractions possessed inhibitory effects on the platelet aggregation induced by arachidonic acid and collagen, and on the vasoconstriction induced by norepinephrine.

From fractions 5-8 rechromatographed on silica gel column, several compounds were further purified. According to their spectral analysis and comparison with the physical constants in the literature (Lu et al., Yakugaku Zasshi 92: 910-917, 1972), four compounds were identified as dicentrine, N-methylnandigerine, N-methylovigerine and dicentrinone.

TABLE 1

| | Platelet Aggregation (%) | | Aortic Contraction (%) | |
|---|---|---|---|---|
| Fraction | Arachidonic acid | Collagen | NE-phasic | NE-tonic |
| Control | 87.6 ± 1.6 | 88.9 ± 1.4 | 100.0 ± 16.8 | 100.0 ± 1.4 |
| 1 | 0.0 ± 0.0*** | 84.1 ± 1.9 | 132.7 ± 12.2 | 96.1 ± 2.7 |
| 2 | spontaneous aggregation | | 130.6 ± 13.7 | 9.18 ± 1.6* |
| 3 | 74.0 ± 2.3*** | 83.5 ± 2.8 | 130.0 ± 21.2 | 94.7 ± 15.5 |
| 4 | 58.2 ± 6.2*** | 79.7 ± 5.0* | 186.6 ± 37.7 | 115.0 ± 14.3 |
| 5 | 0.0 ± 0.0*** | 0.0 ± 0.0** | 25.0 ± 17.7* | 2.1 ± 1.5*** |
| 6 | 0.0 ± 0.0*** | 20.9 ± 8.4*** | 68.9 ± 10.2 | 24.0 ± 4.5*** |
| 7 | 0.0 ± 0.0*** | 0.0 ± 0.0*** | 5.0 ± 3.5** | 1.9 ± 1.3*** |
| 8 | 0.0 ± 0.0*** | 0.0 ± 0.0*** | 0.0 ± 0.0*** | 0.0 ± 0.0*** |

Means ± S.E.M. are presented. *: $P < 0.05$, : $P < 0.01$, *: $P < 0.001$ as compared with the respective control. Concentration: arachidonic acid (100 μM), collagen (10 μg/ml), norepinephrine (NE, 3 μM), each fraction (100 μg/ml).

EXAMPLE 2

Concentration-response curve analysis of norepinephrine- and phenylephrine-induced contraction of rat thoracic aortae was performed for the $\alpha_1$-adrenoceptor antagonism by dicentrine in comparison with prazosin, yohimbine and phentolamine. As shown in Table 2, dicentrine was less potent than prazosin, but was much more potent than phentolamine or yohimbine. In all cases the Schild slopes were not significantly different from 1.0.

TABLE 2

| Agonist | Antagonist | pA$_2$ | slope | r |
|---|---|---|---|---|
| Norepinephrine | Dicentrine | 8.19 ± 0.09 | 0.94 (0.85-1.2) | 0.99 |
| Phenylephrine | Dicentrine | 9.01 ± 0.10 | 0.94 (0.95-1.32) | 0.99 |

TABLE 2-continued

| Agonist | Antagonist | pA$_2$ | slope | r |
|---|---|---|---|---|
| phrine | | | | |
| | Prazosin | 10.60 ± 0.10 | 0.95 (0.94-1.24) | 0.99 |
| | Yohimbine | 6.20 ± 0.05 | 0.84 (0.65-1.03) | 0.99 |
| | Phentolamine | 7.53 ± 0.10 | 0.72 (0.71-1.20) | 0.99 |

Results are given as means ± S.E.M. or the mean with 95% confidence limits in parentheses.

EXAMPLE 3

In washed rabbit platelets, dicentrine inhibited the aggregation induced by arachidonic acid and collagen, but not that by thrombin, as shown in Table 3. At 6 min after the addition of inducer, indomethacin (50 μM) and EDTA (2 mM) were added to stop the reaction, and thromboxane B$_2$ was assayed by RIA kits. Thromboxane formations caused by arachidonic acid, collagen and thrombin were all suppressed by dicentrine.

TABLE 3

| | Aggregation (%) | | Thromboxane B$_2$ (ng/10$^8$ platelets) | |
|---|---|---|---|---|
| Inducer | Control | Dicentrine | Control | Dicentrine |
| Arachidonic acid | 92 ± 1 | 11 ± 7*** | 445 ± 44 | 19 ± 15*** |
| Collagen | 94 ± 1 | 51 ± 7*** | 478 ± 93 | 70 ± 5** |
| Thrombin | 95 ± 2 | 92 ± 2 | 131 ± 25 | 44 ± 14* |

Means ± S.E.M. are presented. *: $P < 0.05$, : $P < 0.01$, *: $P < 0.001$ as compared with the respective control. Concentration: arachidonic acid (100 μM), collagen (10 ug/ml), thrombin (0.1 U/ml), dicentrine (150 μM).

EXAMPLE 4

The effects of dicentrine and quinidine on action potential were compared and studied in rat ventricular cells. As shown in Table 4, cells bathed in Ca$^{++}$-Tyrode, 3 to 5 min exposure to 3 μM dicentrine prolonged the action potential duration (APD$_{50}$) from 59.9±11.3 msec to 201.9±28.7 msec. In addition to the prolongation of APD$_{50}$, a depression of initial upstroke amplitude from 138.3±2.6 mV to 125.5±4.5 mV and prolongation of the time to peak amplitude from 5.0±0.5 msec to 10.0±1.9 msec were observed. For cells treated with 3 μM quinidine, similar effects were obtained.

TABLE 4

| | | AP amplitude (mV) | APD$_{50}$ (msec) | T$_p$ (msec) |
|---|---|---|---|---|
| A. | Control | 138.3 ± 2.6 | 59.9 ± 11.3 | 5.0 ± 0.5 |
| | Dicentrine | 125.5 ± 4.5* | 201.9 ± 28.7* | 10.0 ± 1.9* |
| B. | Control | 135.2 ± 2.2 | 62.6 ± 3.9 | 5.3 ± 0.5 |

TABLE 4-continued

|  | AP amplitude (mV) | APD$_{50}$ (msec) | T$_p$ (msec) |
|---|---|---|---|
| Quinidine | 121.2 ± 2.3* | 276.0 ± 18.6* | 10.8 ± 2.4* |

Means ± S.E.M. are presented. *: P < 0.05 as compared with the respective control.
APD$_{50}$: action potential duration measured at 50% repolarization from the peak amplitude.
T$_p$: time to peak measured from the start of depolarization to the peak of the action potential.
Concentration: dicentrine (3 μM), quinidine (3 μM).

EXAMPLE 5

Effects of dicentrine and prasozin on systemic hemodynamic parameters of pentobarbital-anesthetized rats were compared and shown in Table 5. Dicentrine is resemble to prazosin, another $\alpha_1$-adrenoceptor blocker, both drugs produce similar hemodynamic changes: a decrease in mean arterial pressure (MAP), a reduction in total peripheral resistance by increasing blood flow, little or no change in cardiac output (CO). However, dicentrine produces no change in heart rate (HR), or stroke volume (SV) in comparison with prazosin.

TABLE 5

| Hemo-dynamic Parameters | Dicentrine (1.0 mg/kg) | | Prazosin (0.1 mg/kg) | |
|---|---|---|---|---|
|  | Before | After | Before | After |
| MAP (mm Hg) | 122 ± 5 | 62 ± 5*** | 120 ± 4 | 68 ± 6*** |
| HR (bpm) | 353 ± 10 | 348 ± 8 | 367 ± 9 | 337 ± 10* |
| CO (ml/min) | 21 ± 2 | 25 ± 4 | 27 ± 3 | 32 ± 3 |
| SV (μ/min/beat) | 50 ± 3 | 55 ± 9 | 64 ± 4 | 79 ± 7* |
| Blood flow | 7 ± 4 | 200 ± 27** | 7 ± 4 | 171 ± 14** |

*: p < 0.05; : P < 0.01, *: P < 0.001 before vs. after.

EXAMPLE 6

In rats fed with high cholesterol and high fat diet for three weeks, the blood level of cholesterol increased by two times and triglyceride by 3.5 times, as shown in Table 6. When dicentrine was administered orally twice a day (10 mg/kg) in the last week, the triglyceride level was restored to normal levels, while cholesterol level was unchanged. Prazosin had similar effect at a dose of 5 mg/kg.

TABLE 6

| Treatment | Cholesterol (mg/dl) | Triglyceride (mg/dl) |
|---|---|---|
| 1. Normal diet | 62 ± 4.5$^a$ | 84 ± 5.4$^b$ |
| 2. High cholesterol & fat diet | 120 ± 7.1$^a$ | 305 ± 11.1$^{bcd}$ |
| 3. High cholesterol & fat diet + dicentrine (10 mg/kg) | 112 ± 4.6 | 108 ± 4.3$^c$ |
| 4. High cholesterol & fat diet + prazosin (5 mg/kg) | 112 ± 3.9 | 114 ± 9.2$^d$ | a, b, c, d: data in pair show significant difference (p < 0.001).

EXAMPLE 7

In rats fed with high cholesterol and high fat diet for three weeks, the maximal contractile force of isolated thoracic aorta increased by two times, as shown in Table 7. When dicentrine was administered orally twice a day (10 mg/kg) in the last week, the maximal contractile force of isolated thoracic aorta was restored to normal range. Prazosin had similar effect at a dose of 5 mg/kg.

TABLE 7

| Treatment | Concentration of phenylephrine (M) | | | | |
|---|---|---|---|---|---|
|  | $3 \times 10^{-8}$ | $10^{-7}$ | $3 \times 10^{-7}$ | $10^{-6}$ | $3 \times 10^{-6}$ |
| 1. Normal diet | 0.2 ± 0.04$^a$ | 0.48 ± 0.05 | 0.69 ± 0.10 | 0.86 ± 0.15 | 0.94 ± 0.18 |
| 2. High cholesterol & fat diet | 0.71 ± 0.10 | 1.14 ± 0.10 | 1.55 ± 0.10 | 1.73 ± 0.10 | 1.87 ± 0.10 |
| 3. High cholesterol & fat diet + dicentrine | 0.22 ± 0.05 | 0.55 ± 0.07 | 0.55 ± 0.07 | 0.67 ± 0.11 | 0.75 ± 0.12 |
| 4. High cholesterol & fat diet + prazosin | 0.30 ± 0.05 | 0.51 ± 0.08 | 0.70 ± 0.09 | 0.80 ± 0.12 | 0.87 ± 0.12 |

$^a$contractile force (g); dosage: dicentrine (10 mg/kg), prazosin (5 mg/kg)

What is claimed is:

1. A method for treating hypertension in a subject in need thereof, comprising administering to said subject a pharmaceutical composition which comprises an effective amount of dicentrine or a pharmaceutically acceptable salt thereof and a pharmaceutically acceptable carrier.

2. The method of claim 1, wherein the effective amount is administered intravenously.

3. A method for treating hypertension in a subject in need thereof, comprising orally administering to said subject a pharmaceutical composition which comprises an effective amount of dicentrine or a pharmaceutically acceptable salt thereof and a pharmaceutically acceptable diluent and carrier.

4. A method for treating hypertension in a subject in need thereof, comprising parenterally administering to said subject a pharmaceutical composition which comprises an effective amount of dicentrine or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 5,262,421
DATED : November 16, 1993
INVENTOR(S) : Ming-Jai Su

It is certified that error appears in the above-indentified patent and that said Letters Patent is hereby corrected as shown below:

On the Title page, item [75], inventor's name should read--Ming-Jai Su--.

Signed and Sealed this

Seventh Day of June, 1994

*Attest:*

BRUCE LEHMAN

*Attesting Officer*     *Commissioner of Patents and Trademarks*